(12) United States Patent
Cox et al.

(10) Patent No.: US 6,352,697 B1
(45) Date of Patent: *Mar. 5, 2002

(54) SAPONIN PREPARATIONS AND USE THEREOF IN ISCOMS

(75) Inventors: John Cooper Cox, Bullengarook; Alan Robert Coulter, Glen Iris, both of (AU); Bror Morein, Uppsala (SE); Karin Lovgren-Bengtsson, Uppsala (SE); Bo Sundquist, Uppsala (SE)

(73) Assignee: Iscotec A.B., Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,987

(22) PCT Filed: Oct. 12, 1995

(86) PCT No.: PCT/AU95/00670

§ 371 Date: Feb. 22, 1999

§ 102(e) Date: Feb. 22, 1999

(87) PCT Pub. No.: WO96/11711

PCT Pub. Date: Apr. 25, 1996

(30) Foreign Application Priority Data

Oct. 12, 1994 (AU) .............................. PM8732

(51) Int. Cl.$^7$ .............................................. A61K 45/00
(52) U.S. Cl. ................ 424/278.1; 424/278.1; 424/283.1; 424/184.1; 514/885
(58) Field of Search ................ 424/184.1, 278.1, 424/283.1; 514/885

(56) References Cited

FOREIGN PATENT DOCUMENTS

| WO | WO 88/09336 | 12/1988 |
|----|-------------|---------|
| WO | WO 90/03184 | 4/1990 |
| WO | WO 92/06710 | * 4/1992 |
| WO | WO 93/05789 | 4/1993 |
| WO | WO 94/01118 | 1/1994 |
| WO | WO 95/09179 | 4/1995 |

OTHER PUBLICATIONS

Cox, J.C. and Coulter, A.R. (1992) "Advances in Adjuvant Technology and Application" in Animal Parasite Chapter 4, pp. 68–79, W.K. Young, Ed., CRC Press.

Kensil, C.R. et al., Separation and characterization of saponins with adjuvant from Quillaja saponaria 1991 (146) 431–437 Journal of Immunology.

* cited by examiner

Primary Examiner—Patrick J. Nolan
Assistant Examiner—Gerald R. Ewoldt
(74) Attorney, Agent, or Firm—Foley & Lardner

(57) ABSTRACT

Saponin preparations based on defined compositions of purified saponin fractions derived from the bark of *Quillaja saponaria* Molina are disclosed. The saponin preparations are useful in immunostimulating complex (iscom) matrices. The saponin preparations, and iscom matrices prepared using them, have particular activity as adjuvants.

16 Claims, 8 Drawing Sheets

SAPONIN PREPARATIONS AND USE THEREOF IN ISCOMS

Figure 1:
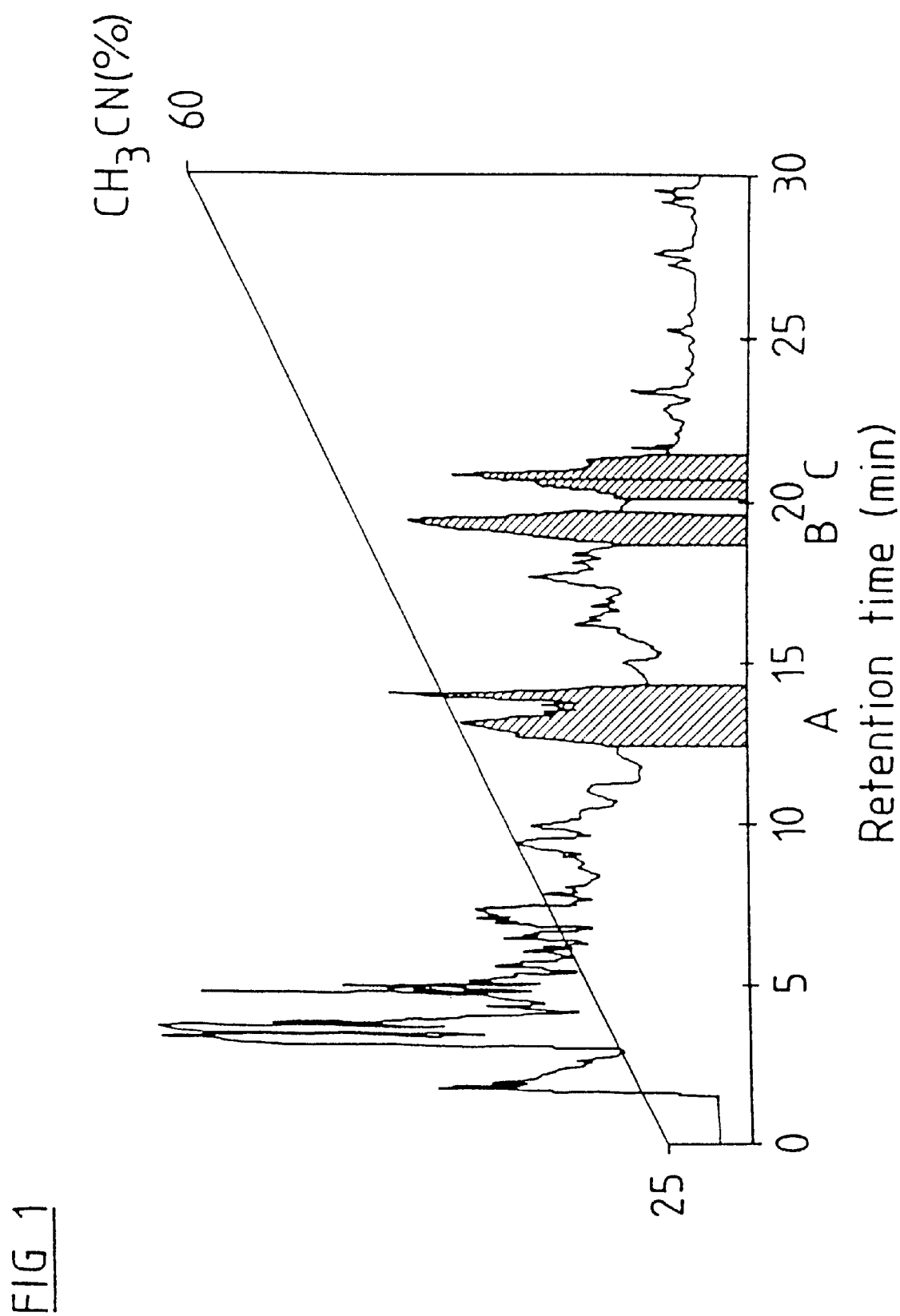
Figure 2A:
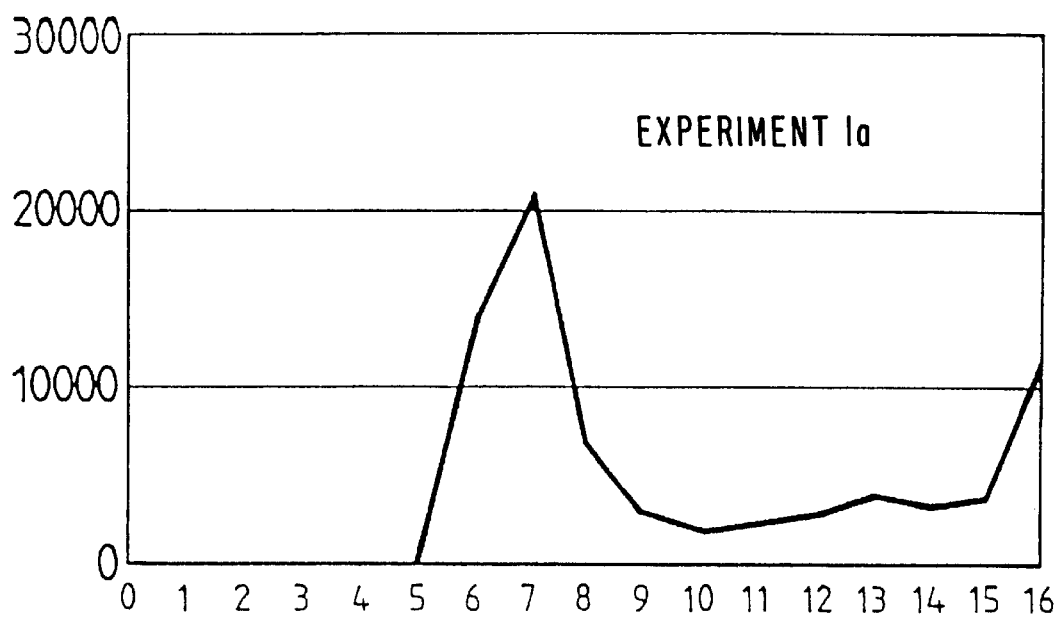
Figure 2B:
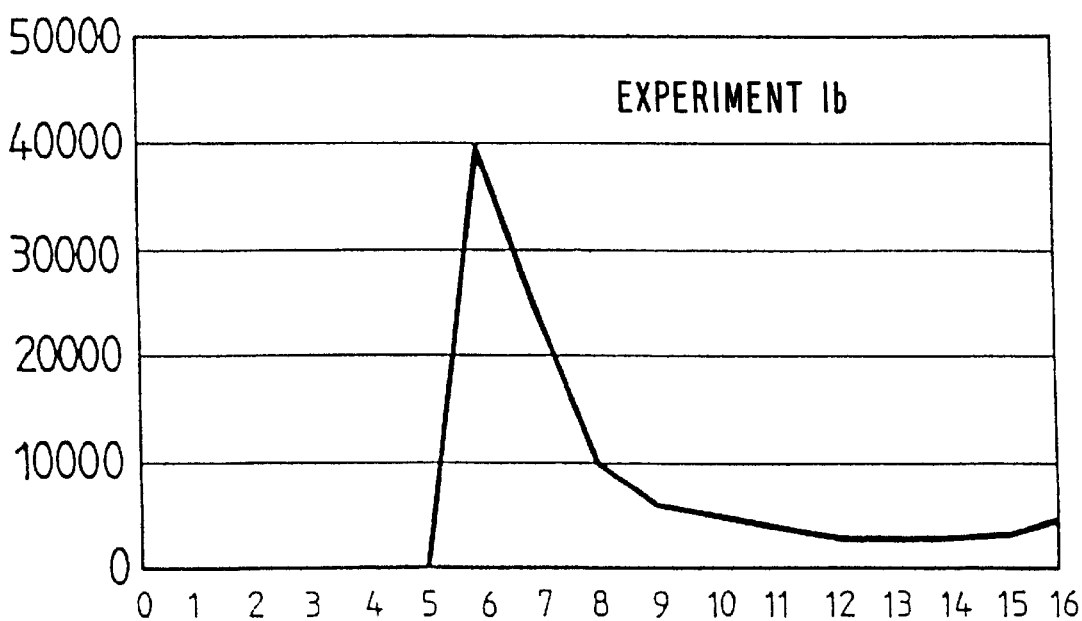
Figure 2C:
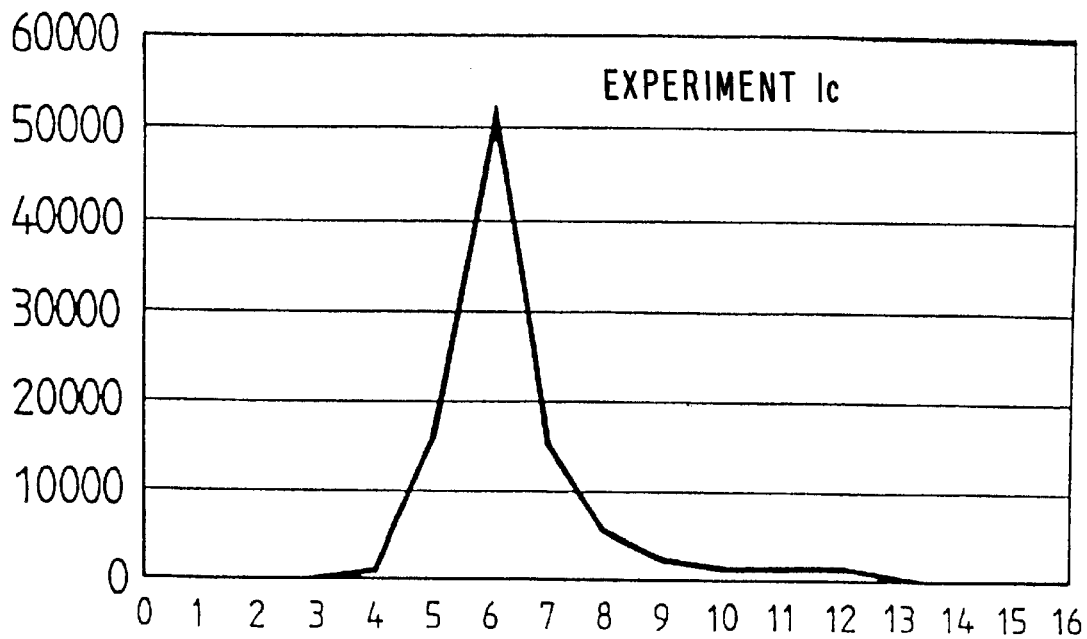
Figure 2D:
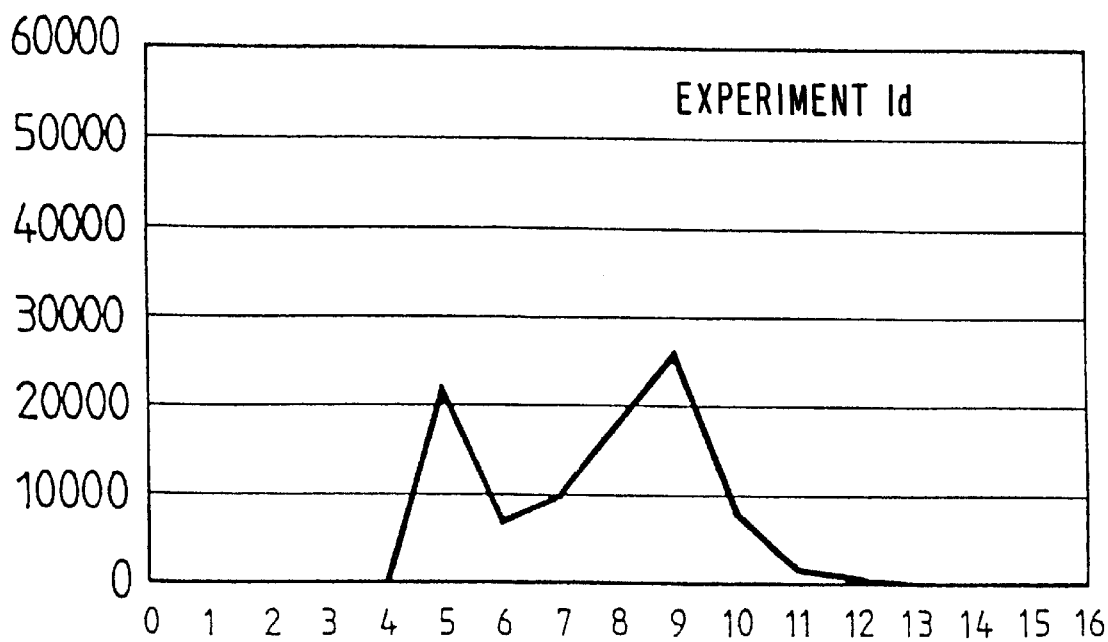
Figure 3A:
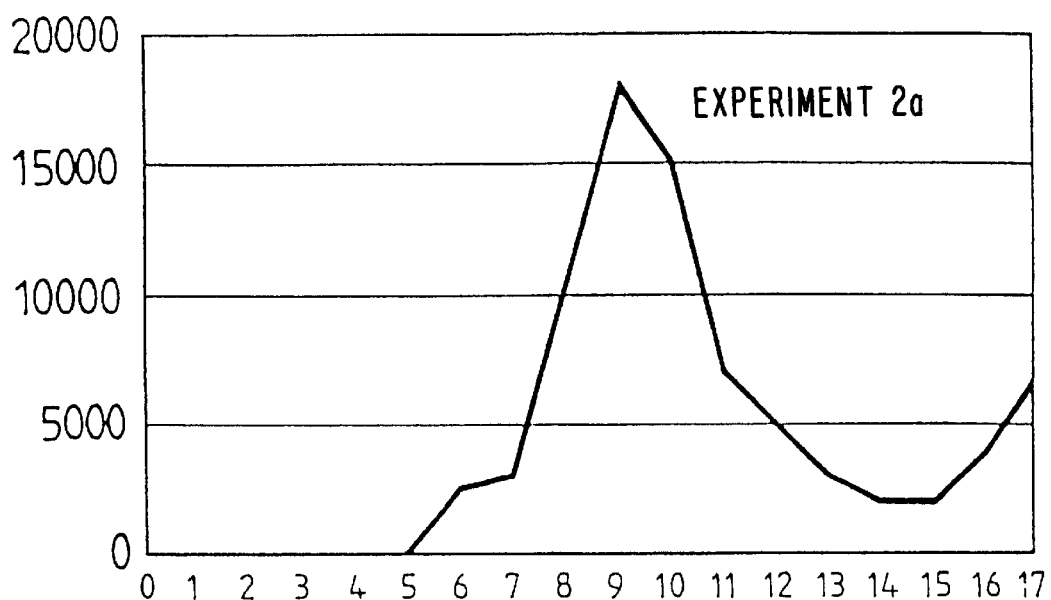
Figure 3B:
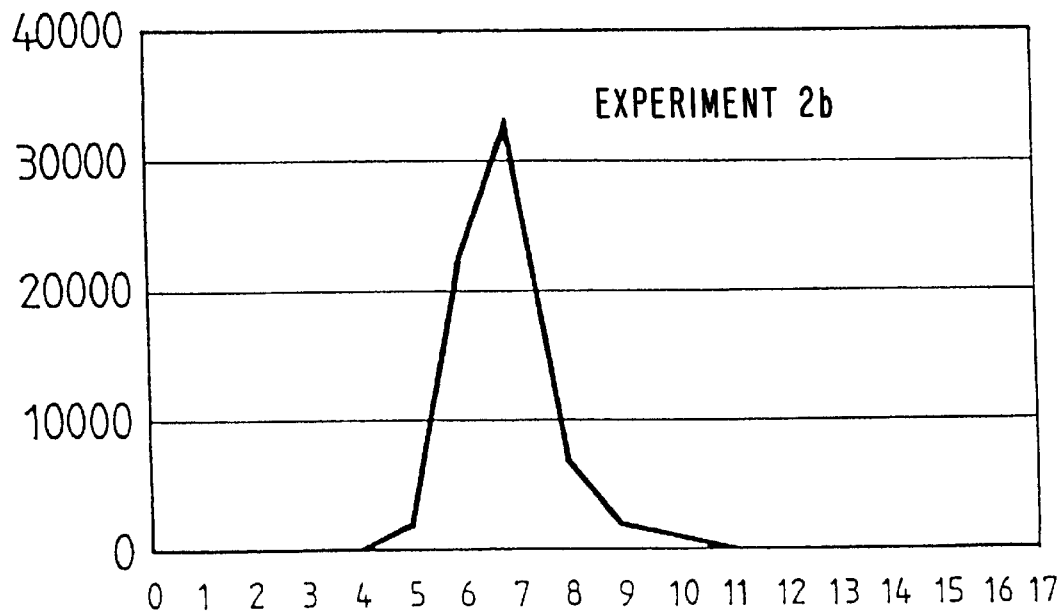
Figure 3C:
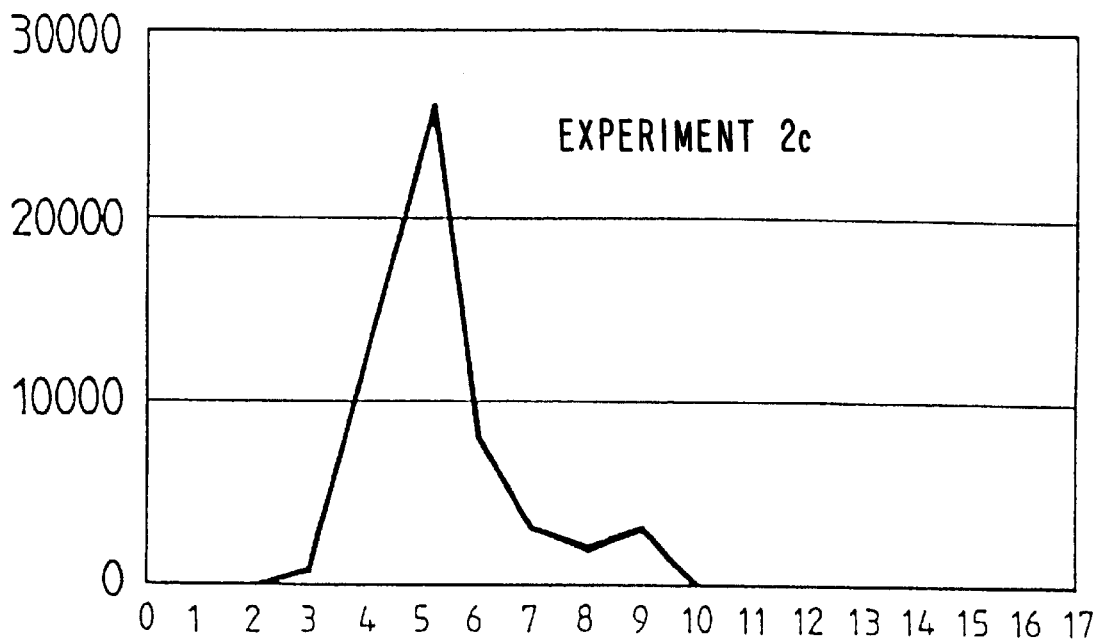
Figure 3D:
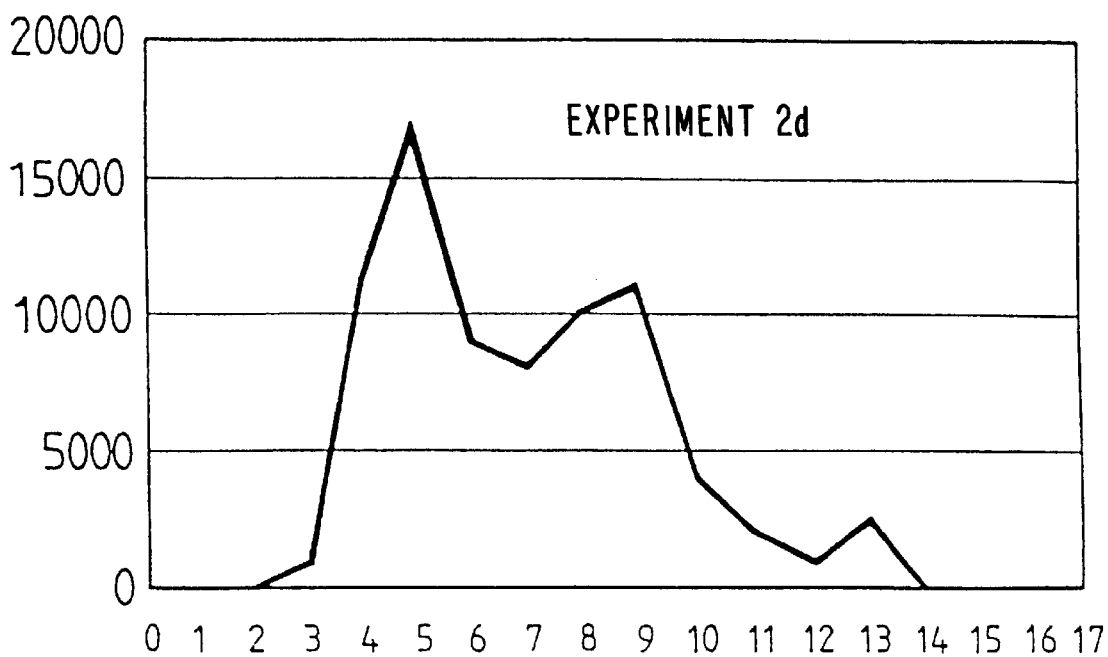
Figure 4A:
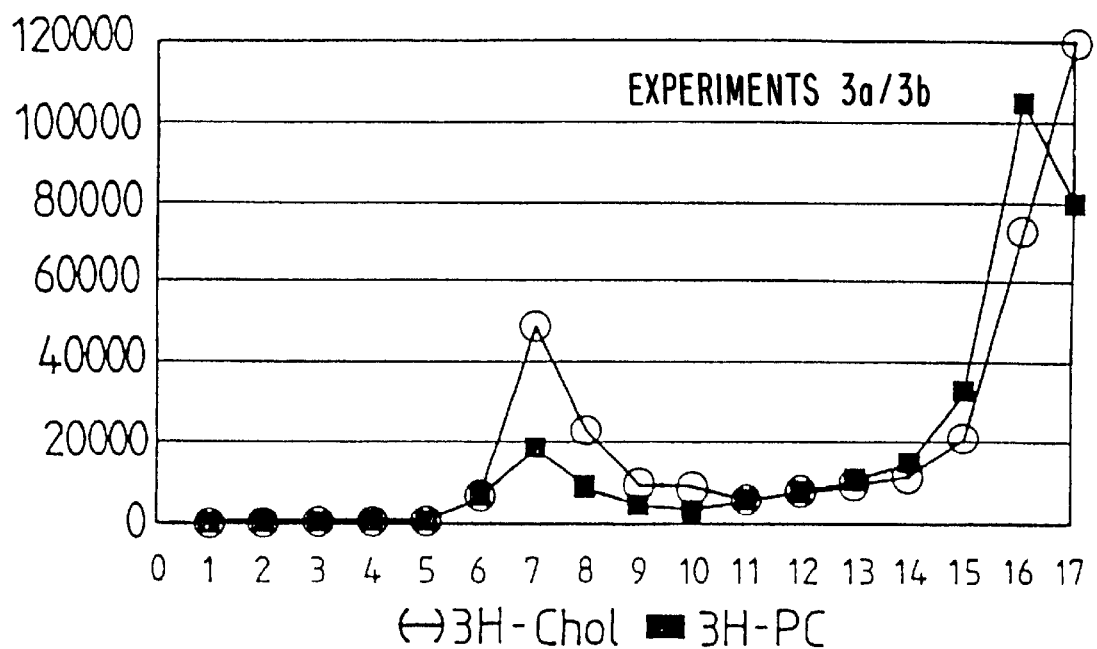
Figure 4B:
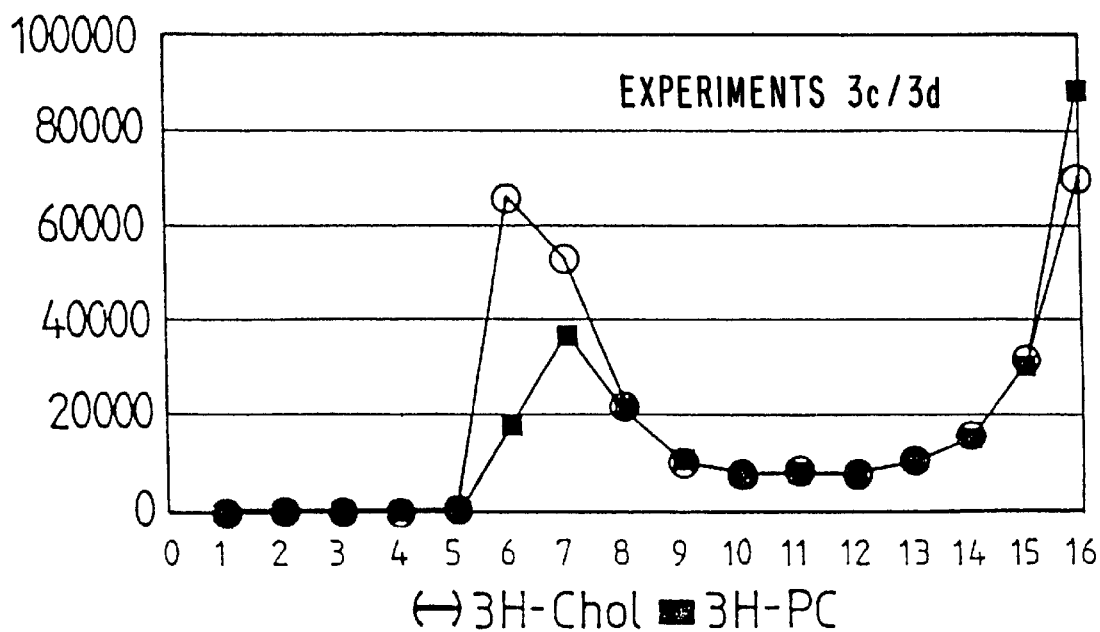
Figure 4C:
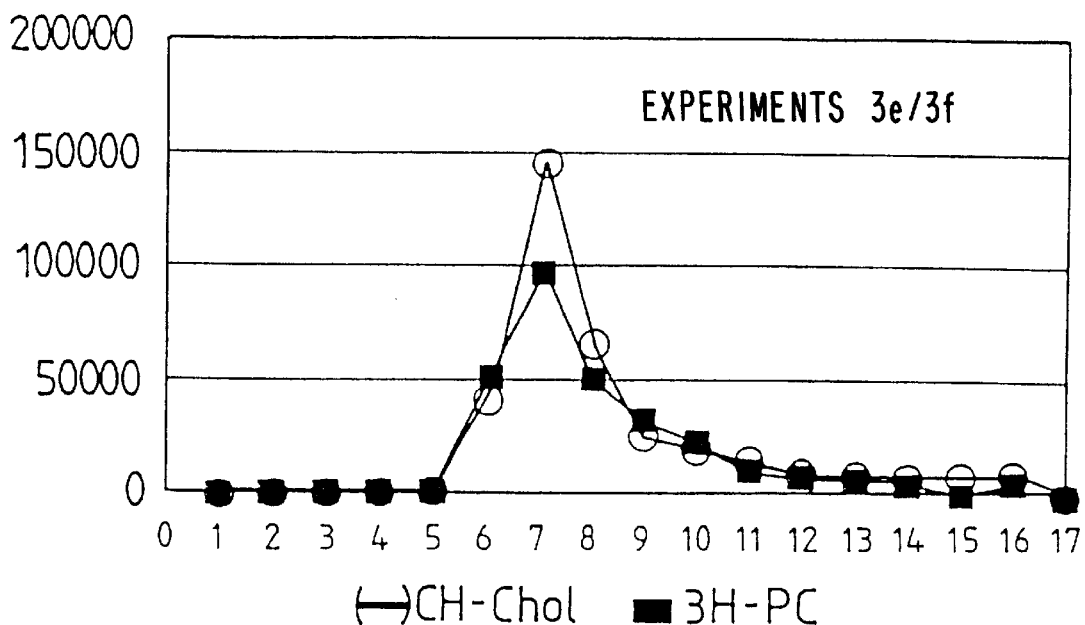
Figure 4D:
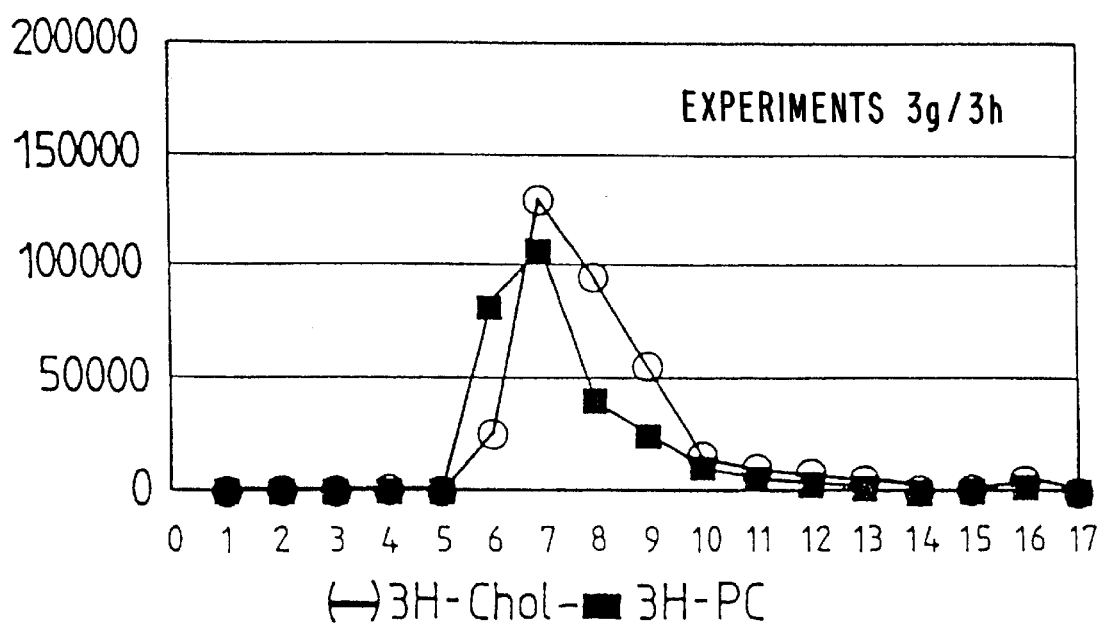

This application is a 371 national stage application of PCT/AU95/00670, filed Oct. 12, 1995.

FIELD OF THE INVENTION

This invention relates to saponin preparations, particularly to saponin preparations based on defined compositions of purified saponin fractions derived from the bark of *Quillaja saponaria* Molina. The invention also extends to immunostimulating complex (iscom) matrices prepared using these saponin preparations, as well as to immunogenic iscoms in which immunogens are incorporated into or associated with an iscom matrix. Such immunogens will usually be proteins or peptides derived from bacteria, viruses or other microorganisms, but they may, in addition, be any other protein, peptide or other chemical entity which can induce an immune response.

The saponin preparations of this invention, and iscom matrices prepared using them, have particular activity as adjuvants, that is as products which result in a specific increase in the immunogenicity of a vaccine component

BACKGROUND OF THE INVENTION

The adjuvant properties of saponin have been long known as has its ability to increase antibody titres to immunogens. As used herein the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree *Quillaja saponaria* Molina. Saponin from this source was used to isolate a "homogeneous" fraction denoted "Quil A" (Dalsgaard, 1974).

Acute toxicity is a major concern for both the veterinary and human use of Quil A in vaccine preparations. One way to avoid the acute toxicity of Quil A is the use of iscoms, an abbreviation for Immuno Stimulating COMplexes. This is primarily because Quil A is less toxic when incorporated into iscoms, because its association with cholesterol in the iscom reduces its affinity for cholesterol in cell membranes and hence its cell lytic effects. In addition, a lesser amount of Quil A is required to generate a similar level of adjuvant effect. Iscoms are small, cage-like structures generally 30 to 40 nm in diameter which retain this structure on freeze drying. The final formulation of a typical immunogenic iscom with an optimal amount of immunogenic protein is a weight ratio of Quil A, cholesterol, phosphatidyl choline, and protein (1:1:1:5). Such a typical iscom is estimated to contain 5 to 10% by weight Quil A, 1 to 5% cholesterol and phospholipids, and the remainder protein. Peptides can be incorporated into iscoms either directly or by chemical coupling to a carrier protein (e.g. influenza envelope protein) after incorporation of the carrier protein into iscoms.

As an adjuvant, the iscom confers many advantages including powerful immunostimulatory effects, low toxicity, ability to induce both cellular (including CTL) and humoral responses, and it is inexpensive in both reagent and manufacturing cost. However, in the past, iscoms have had two major disadvantages; firstly, the Quil A used in their preparation was a complex and ill defined mixture of a biologically-derived product, and batch-to-batch variation was therefore to be expected; and secondly, iscoms still showed injection-site reactivity and low but detectable in vivo toxicity.

Since the recognition of the adjuvant activity of Quil A (Dalsgaard, 1974) several groups have further fractionated this material into a number of "purified" components (Morein et al., Australian Patent Specification No. 632067; Kersten, 1990; Kensil, 1988; Kensil 1991). These components were subsequently shown to have variable properties especially in regards to adjuvant activity, haemolytic activity and ability to form iscoms. The use of purified Quil A components conferred two potential advantages for their use in a human vaccine. Firstly, the purified component could be characterized and therefore made reproducibly; and secondly, the components could be selected for optimal usefulness.

The immunomodulatory properties of the Quil A saponins and the additional benefits to be derived from these saponins when they are incorporated into an iscom have been described in various publications, e.g. Cox and Coulter, 1992; Dalsgaard, 1974; Morein et al., Australian Patent Specifications Nos. 558258, 589915, 590904 and 632067. In Australian Patent Specification No. 632067, the separation of a preparation of Quil A into three distinct fractions called B4B, B3 and B2 is described, along with HPLC chromatographic procedures for this fractionation. More carefully defined and controllable procedures for the fractionation of Quil A have now been devised which result in three major fractions with increasing degrees of hydrophobicity in the purification system used.

In work leading to the present invention, it has now been shown that saponins derived from *Quillaja saponaria* can be separated into fractions with differing chemical and biological properties, including the important biological properties of adjuvant activity, haemolytic activity, ability to form iscoms and in vivo toxicity, and that particular compositions of these fractions can be prepared to form novel saponin preparations which are capable of forming good iscoms, having optimal adjuvant activity but minimal haemolytic and toxic activity.

SUMMARY OF THE INVENTION

According to the present invention, there is provided a saponin preparation comprising saponins of *Quillaja saponaria*, said preparation comprising from 50 to 90% by weight of Fraction A of Quil A (as herein defined) and from 50% to 10% by weight of Fraction C of Quil A (as herein defined).

Preferably, the saponin preparation comprises from 50% to 70% by weight of Fraction A and from 50% to 30% by weight of Fraction C. A particularly preferred preparation comprises about 70% by weight of Fraction A and about 30% by weight of Fraction C.

The term "Quil A" is used throughout this specification and in the claims as a generic description of a semi-purified saponin fraction of *Quillaja saponaria*.

The saponin preparation may, if desired, include minor amounts (for example up to 40% by weight) of other adjuvant materials with desired immunomodulatory properties, including minor amounts of Fraction B of Quil A or of other saponins. Examples of other saponins or other adjuvant materials which are suitable for inclusion in this preparation are described in Australian Patent Specification No. 632067, incorporated herein by reference.

As described above, it is known that in order to prepare an immunostimulating complex (iscom) matrix, Quil A, a sterol such as cholesterol and optionally a lipid such as phosphatidyl choline, must be included in the reaction mixture.

In accordance with another aspect of the present invention there is provided an immunostimulating complex (iscom) matrix comprising a saponin preparation, a sterol and optionally a lipid, wherein the saponin preparation comprises from 50 to 90% by weight of Fraction A of Quil A (as herein defined) and from 50% to 10% by weight of Fraction C of Quil A (as herein defined).

Preferably, in such an iscom matrix the sterol is cholesterol, and the lipid (which is optionally present) is a phospholipid such as phosphatidyl choline.

In yet another aspect, this invention provides an immunogenic iscom which comprises an iscom matrix as described above having at least one immunogen incorporated into or associated with the iscom matrix.

An iscom matrix or an immunogenic iscom in accordance with the present invention may be prepared by techniques which are well known to persons skilled in the art, and which are described in detail in the publications Cox and Coulter, 1992 and Morein et al., Australian Patent Specifications Nos. 558258, 589915, 590904 and 632067, the disclosures of which are incorporated herein by reference.

The immunogen which is incorporated into or associated with the iscom matrix in accordance with this invention may be any chemical entity which can induce an immune response in an individual such as (but not limited to) a human or other animal, including but not limited to a humoral and/or cell-mediated immune response to bacteria, viruses or other microorganisms.

The specific immunogen can be a protein or peptide, a polysaccharide, a lipopolysaccharide or a lipopeptide; or it can be a combination of any of these. Particularly, the specific immunogen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product. Examples of such immunogens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, haemophilias influenza, chlamydia, varicella-zoster virus, rabies or human immunodeficiency virus.

The present invention also extends to a vaccine composition comprising as the active component thereof either (i) an immunogenic iscom as broadly described above or (ii) an iscom matrix as broadly described above and at least one immunogen, together with one or more pharmaceutically acceptable carriers and/or diluents.

The formulation of such vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect, the present invention extends to a method of eliciting or inducing an immune response in an individual, which comprises administering to the individual an immunologically effective amount of a vaccine composition as broadly described above.

As previously mentioned, the individual may be a human or other animal, including a livestock animal (eg. sheep, cow or horse), laboratory test animal (eg. mouse, rat, rabbit or guinea pig), companion animal (eg. dog or cat) or wild animal.

An immunologically effective amount means that amount necessary at least partly to attain the desired immune response, or to delay the onset of, inhibit the progression of, or halt altogether, the onset or progression of the particular condition being treated. This amount varies depending upon the health and physical condition of the individual to be treated, the taxonomic group of individual to be treated, the capacity of the individual's immune system to synthesize antibodies, the degree of protection desired, the formulation of the vaccine, the assessment of the medical situation, and other relevant factors. It is expected that the amount will fall in a relatively broad range that can be determined through routine trials.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

The purification of crude aqueous Quil A extract to Fractions A, B and C of Quil A is described in detail in Example 1 hereinafter. It should be understood that this purification procedure is included by way of example only, and that fractions functionally similar or equivalent to Fractions A, B and C can be prepared by diverse other chromatographic procedures.

For the purposes of identification of Fractions A, B and C referred to herein, reference may be made to the purification procedure of Example 1. In general terms, in this procedure Fractions A, B and C are prepared from the lipophilic fraction obtained on chromatographic separation of the crude aqueous Quil A extract and elution with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is, or corresponds to, the fraction which is eluted at approximately 39% acetonitrile. The fraction referred to herein as "Fraction B" or "QH-B" is, or corresponds to, the fraction which is eluted at approximately 47% acetonitrile. The fraction referred to herein as "Fraction C" or "QH-C" is, or corresponds to, the fraction which is eluted at approximately 49% acetonitrile.

When prepared as described herein, Fractions A, B and C of Quil A each represent groups or families of chemically closely-related molecules with definable properties. The chromatographic conditions under which they are obtained are such that the batch-to-batch reproducibility in terms of elution profile and biological activity is highly consistent.

Fractions A, B and C as described above have been studied for their adjuvant activity, haemolytic activity and ability to form iscoms, and the results are summarized in Table 1:

TABLE 1

Properties of Fractions A, B and C of Quil A.

| Fraction | Adjuvant Activity | Haemolytic activity | Iscom-forming ability |
|---|---|---|---|
| A | medium | very low | very high |
| B | very high | very high | medium |
| C | high | high | medium |

Surprisingly, it has now been found that particular combinations of Fractions A and C, more particularly combinations of from 50 to 90% by weight of Fraction A with from 50 to 10% by weight of Fraction C (with 0% of Fraction B), result in a saponin preparation which has the desirable properties of A (good 5 iscom formation and low haemolytic activity) and the benefits of C (good adjuvant activity). In one particularly preferred saponin preparation of this invention, the ratio of 7 parts A: 0 parts B: 3 parts C (=7,0,3; or QH703) has been found to provide very good adjuvant activity, to form iscoms easily yet to have a much lower haemolytic activity than would be expected from the component fractions. It is to be understood, however, that the present invention extends to other saponin preparations ranging from 5 parts A: 0 parts B; 5 parts C (=5,0,5; or QH505) to 9 parts A: 0 parts B; 1 part C (=9,0,1; or QH901).

The following Examples describe a method for the purification of A, B, and C; and compare pure A (10,0,0), pure B (0,10,0), pure C (0,0,10) and the mixture QH703 (7,0,3) in terms of adjuvant activity, haemolytic activity, ease of iscom formation and induction of IL-1, a marker for immunomodulatory activity. Data is also included to demonstrate the pre-clinical safety profile of the saponin preparation of this invention and iscom matrix made therefrom, as well as the clinical safety of this iscom matrix. The overall conclusions from this data is that a mixture of A and C, roughly in the ratio 7:3 (=7,0,3; or QH703) is an optimal ratio of purified saponins from which to form iscom matrix or immunogenic iscoms.

Further features of the present invention are more fully described in the following Example(s). It is to be understood, however, that this detailed description is included solely for the purposes of exemplifying the present invention, and should not be understood in any way as a restriction on the broad description of the invention as set out above.

Figure 5:
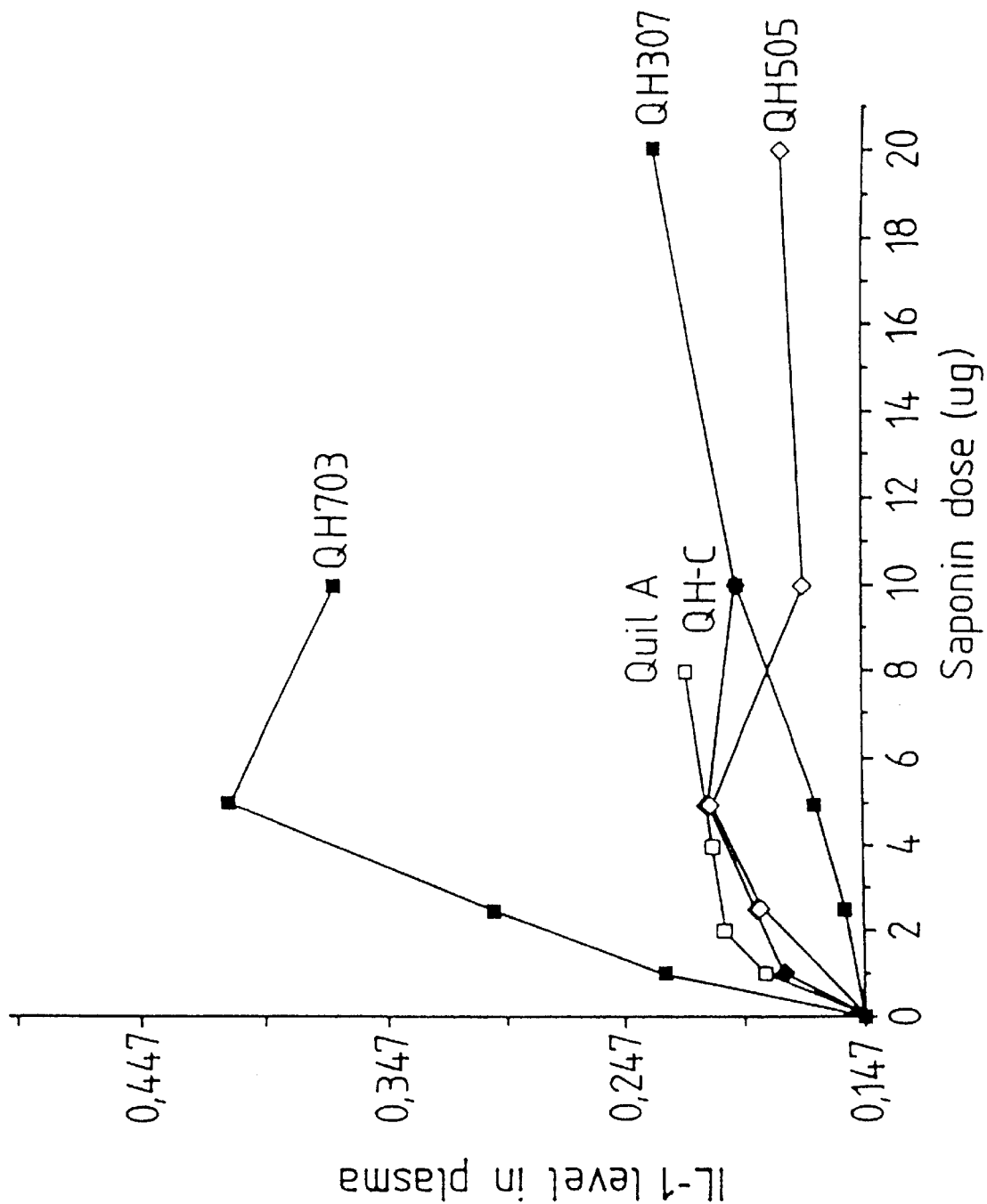

In the accompanying drawings:

FIG. 1 shows the preparation of fractions A, B and C by HPLC;

FIGS. 2A–D, 3A–D, and 4A–D show sucrose gradient elution profiles in preparation of iscom matrix; and FIG. 5 shows plasma IL-1 levels in mice following dosing with various quantities and compositions of Quil A and fractions thereof.

EXAMPLE 1

Purification of Crude Quil A Extract to Fractions A, B and C

A solution (0.5 ml) of crude Quillaja bark extract in water (0.5 g/ml) is pretreated on a SEP-PAK™ column (Waters Associates, Mass.).

The pretreatment involves washing of the loaded sep-pak column with 10% acetonitrile in acidic water in order to remove hydrophilic substances. Lipophilic substance s including QH-A, QH-B and QH-C are then eluted by 70% acetonitrile in water.

The lipophilic fraction from the SEP-PAK™ column is then separated by a semipreparative HPLC column (CT-sil, C8, 10×250 mm, ChromTech, Sweden). The sample is eluted through the column by a gradient from 25% to 60% acetonitrile in acidic water. Three fractions are collected from the HPLC column during the separation. The residues after evaporation of these three fractions constitute QH-A, QH-B and QH-C.

The fractions designated QH-A, QH-B and QH-C were eluted at approximately 39, 47 and 49% acetonitrile respectively. The exact elution profile and conditions are shown in FIG. 1.

EXAMPLE 2

Formation of Iscoms with Purified QH-A, QH-B and QH-C, Either Alone or in Combination Subunits of iscoms result from the interaction of Quillaja saponins and cholesterol. Phospholipids are then involved in the assembly of the subunits into the iscom matrix structure. A typical reaction mixture for the preparation of iscom matrix is 5 mg/ml Quil A and 1 mg/ml each for cholesterol and phospholipid. The following experiments were performed to determine the optimal reaction conditions for various Quil A fractions. The assumption behind these experiments is that the more stable the interaction between Quil A and cholesterol/phospholipid, the better suited the structure will be to incorporate immunogens without disruption and concomitant increased haemolytic activity.

MATERIALS

Cholesterol and $^3$H-cholesterol (4211 cpm/ug)
10 mg/ml (w/v) in 20% MEGA -10 (w/w) in $H_2O$
Phosphatidyl choline and $^3$H-phosphatidyl choline
10 mg/ml (w/v) in 20% MEGA-10 (w/w) in $H_2O$
QH-A and QH-C
100 mg/ml (w/w) in $H_2O$
PBS
Dialysis tubing, MW cut off 12–14.000

Method

Reaction mixtures were setup as shown in Tables 2 and 3 and incubated for 2 h at room temperature prior to extensive dialysis against PBS at room temperature.

All samples were then subjected to Sucrose gradient centrifugation, 10–50% (w/w) sucrose, 200.000×g (Raver), 10° C., 18 h, 11.4 ml tubes (Rotor TST 41.14 eq to SW-40)

The sucrose gradient profiles are shown in FIGS. 2 to 4 for experiments 1 to 3 respectively.

The conclusions from these experiments are summarized below:

Exp 1a–d

The ratio of Cholesterol:QH-A giving a homogenous preparation of matrix is 1c, i.e., the one made with an initial ratio of CHOL:QHA=1:4 (prior to dialysis), giving a 1:2 ratio in the isolated final product. The mixtures with a higher ratio of CHOL (1a–b) produced opalescent-slightly opalescent preparations in which not all cholesterol is bound by the QH. The preparation with lower CHOL:QHA ratio (1d) did not give rise to a homogenous preparation of matrix, this preparation contained a lot of small fragments (upper peak).

Exp 2a–d

The ratio of cholesterol:QH-C giving a homogenous preparation of matrix is 2b, i.e., the one made with an initial ratio of CHOL:QHC=1:2 (prior to dialysis), giving a 1:1.4 ratio in the isolated final product. The mixture with a higher ratio of CHOL (2a-) produced opalescent preparation in which not all cholesterol is consumed by the QH. The preparation with lower CHOL:QHC ratio (2c–d) did not give rise to homogenous preparations of matrix, preparation 2c contained some small fragments (upper peak) and preparation 2d a considerable amount of fragments.

Exp 3a–d

In this experiment the same amounts of QH-A and cholesterol were mixed as in EXP 1a–d but PC was also included in amounts equal to CHOL.QH Double mixtures were prepared with either CHOL or PC labelled ($^3$H). As shown in the FIGS. 3a–d the ideal ratio of CHOL:QHA is not affected still the initial ratio in the mixture should be 1:4 (3c) but PC helps to keep the complex together in exp 3d compared to 1d.

From the above, two conclusions can be drawn.

i) the ratio of lipid and cholesterol to QH is optimal at 1:4 through to 1:5.

ii) the mixture of QH-A and QH-C which will most accurately balance the ratios of cholesterol to QH so that neither cholesterol nor QH is in excess is QH703. For example, if a 1:5 ratio is used, then chol:QH-A ratio is 1:3.5 and chol:QH-C is 1:1.5, both very close to the optimal ratios determined in experiments 1 and 2.

TABLE 2

Incubation ratios for preparing iscom matrix for experiments 1 and 2.

| | QH-A | QH-C | 3H-CHOL | PBS |
|---|---|---|---|---|
| 1a | 0.5 mg (5 µl) | | 0.5 mg (50 µl) | 445 µl |
| 1b | 1.0 mg (10 µl) | | 0.5 mg (50 µl) | 440 µl |
| 1c | 2.0 mg (20 µl) | | 0.5 mg (50 µl) | 430 µl |
| 1d | 3.0 mg (30 µl) | | 0.5 mg (50 µl) | 420 µl |
| 2a | | 0.5 mg (5 µl) | 0.5 mg (50 µl) | 445 µl |
| 2b | | 1.0 mg (10 µl) | 0.5 mg (50 µl) | 440 µl |
| 2c | | 2.0 mg (20 µl) | 0.5 mg (50 µl) | 430 µl |
| 2d | | 3.0 mg (30 µl) | 0.5 mg (50 µl) | 420 µl |

TABLE 3

Incubation ratios for preparing iscom matrix for experiment 3.

| | QH-A | 3H-CHOL | CHOL | 3H-PC | PC | PBS |
|---|---|---|---|---|---|---|
| 3a | 0.5 mg (5 µl) | 0.5 mg (50 µl) | | | 0.5 mg (50 µl) | 395 µl |
| 3b | 0.5 mg (5 µl) | | 0.5 mg (50 µl) | 0.5 mg (50 µl) | | 395 µl |
| 3c | 1.0 mg (10 µl) | 0.5 mg (50 µl) | | | 0.5 mg (50 µl) | 390 µl |
| 3d | 1.0 mg (10 µl) | | 0.5 mg (50 µl) | 0.5 mg (50 µl) | | 390 µl |
| 3e | 2.0 mg (20 µl) | 0.5 mg (50 µl) | | | 0.5 mg (50 µl) | 385 µl |
| 3f | 2.0 mg (20 µl) | | 0.5 mg (50 µl) | 0.5 mg (50 µl) | | 385 µl |
| 3g | 3.0 mg (30 µl) | 0.5 mg (50 µl) | | | 0.5 mg (50 µl) | 380 µl |
| 3h | 3.0 mg (30 µl) | | 0.5 mg (50 µl) | 0.5 mg (50 µl) | | 380 µl |

EXAMPLE 3

Immunogenicity and Efficacy Studies on Influenza Virus Iscoms Formed From QH-A, QH-B, QH-C and QH703

Aim: To determine the relative efficacy of various combinations of 'Quil A human' (QH) components A, B and C in Iscoms.

Experimental Conditions

1. Quil A components A, B and C supplied in powder form.
2. Iscoms were made of QH components A, B and C in the following formulations; (a) 10:0:0, (b) 0:10:0, (c) 0:0:10, or (d) 7:0:3.

Preparation of iscom-matrix and protein-iscoms

The following solutions are prepared:

20% w/w mega 10 in distilled water 10 mg/ml cholesterol together with 10 mg/ml egg PC in 20% mega-10 100 mg/ml QH703 in pH 6.2 phosphate buffered Saline Where protein iscoms are being made, the protein to be incorporated should be at about 0.75mg/ml.

Method

To 0.8 ml of phosphate buffered saline (PBS), pH7.4 (in the case of iscom matrix) or 0.8 ml of 0.75 mg/ml protein in PBS, pH7.4 (in the case of protein-iscoms).

Add 80 µl of cholesterol/egg PC in mega-10, mix.

Add 40 µl of 100 mg/ml QH703, mix.

Stir overnight at room temperature (22–24° C.).

Dialyse against PBS, pH7.4 for 4 hours at room temperature, followed by 4 hours against pH 6.2 PBS.

Finally dialyse against pH6.2 PBS at 4° C.

3. Vaccines were prepared using 0.1 µg or 1.0 µg influenza virus HA per dose, and 6 µg or 15 µg of QH per dose. The strain used was a mouse virulent strain of A/PR/8/34.

4. Mice were 6–8 weeks of age, 15 per group Balb/C mice were used for all groups.
5. Mice received 0.1 ml dose, subcut. on the back. They were weighed at 0 time, and at 3 and 7 days post-primary immunisation.
6. All mice were bled at 4 weeks post-primary immunisation.
7. Mice in groups 1a–21a (5 mice/group) were boosted at this time (4 weeks) and bled 7–10 days later.
8. Groups 1–21 were challenged by aerosol challenge at 5 weeks. Groups 1a–21a were not challenged.
9. Primary and secondary bleeds were assayed for antibody response to whole virus.

The results are shown in Table 4. It can be seen that influenza virus HA incorporated into iscoms made from pure QH-A=10, 0, 0 (groups 1 to 4) were generally less immunogenic than those made from a mixture of 7 parts QH-A and 3 parts QH-C=7, 0, 3 (groups 13–16). Primary titres for group 4 were significantly lower ($p>.01$) than those for group 16. These iscom preparations were also less protective as shown by less than 100% protection on subsequent challenge. Significant weight loss was also shown by survivors in group 1; the extent of weight loss being a further indicator of the level of protection afforded by vaccination.

Similarly, primary titres for groups 14 and 16 were significantly higher than those for groups 10 and 12 respectively. QH703 at 6 μg/dose was also at least as effective as whole Quil A at 10 μg/dose (compare groups 13 and 17).

In summary, these experiments show that the use of QH703 permits at least the same immunogenicity and efficacy as shown by the more toxic fractions of Quil A but with a much lower level of those toxic components.

TABLE 4

Immunogenicity and efficacy results for QH iscoms in mice.

QH ISCOM

| Grp No. | QH Formula | Dose QH (μg) | Dose HA (μg) | Median Titer (Range) 1[a] | 2[b] | Weight[c] Change % | | Survivors[c] % |
|---|---|---|---|---|---|---|---|---|
| 1 | 10:0:0 | 6 | 0.1 | 6 (0–1049) | 57 (2–1488) | −15.2 | | 70 |
| 2 | 10:0:0 | 6 | 1 | 19 (0–650) | 187 (68–980) | −1.3 | | 90 |
| 3 | 10:0:0 | 15 | 0.1 | 9 (0–597) | 58 (28–337) | −7.2 | | 100 |
| 4 | 10:0:0 | 15 | 1 | 27 (2–209) | 536 (444–722) | −2.4 | | 100 |
| 5 | 0:10:0 | 6 | 0.1 | 27 (0–490) | 245 (9–523) | −6.7 | | 90 |
| 6 | 0:10:0 | 6 | 1 | 52 (8–653) | 389 (78–2945) | −2.2 | | 100 |
| 7 | 0:10:0 | 15 | 0.1 | 57 (0–748) | 352 (0–971) | −2.4 | | 100 |
| 8 | 0:10:0 | 15 | 1 | 72 (15–317) | 805 (331–1279) | −1.8 | | 100 |
| 9 | 0:0:10 | 6 | 0.1 | 17 (0–914) | 53 (23–104) | −9 | | 100 |
| 10 | 0:0:10 | 6 | 1 | 11 (0–183) | 131 (12–977) | −2.9 | | 100 |
| 11 | 0:0:10 | 15 | 0.1 | 41 (6–380) | 389 (180–2650) | −5.1 | | 100 |
| 12 | 0:0:10 | 15 | 1 | 41 (6–380) | 1327 (342–2052) | −2.3 | | 100 |
| 13 | 7:0:3 | 6 | 0.1 | 40 (2–681) | 697 (121–812) | −2.4 | −6 | 100 |
| 14 | 7:0:3 | 6 | 1 | 62 (2–302) | 327 (163–1714) | 0 | −0.4 | 100 |
| 15 | 7:0:3 | 15 | 0.1 | 38 (10–759) | 563 (105–1906) | −3.7 | −2.6 | 100 |
| 16 | 7:0:3 | 15 | 1 | 96 (7–424) | 870 (463–1887) | −2 | −0.9 | 100 |

CONTROLS

| Grp No. | Vaccine Formulation | Challenge | Dose HA (μg) | Median Titer (Range) 1[a] | 2[b] | Weight[c] Change % | % |
|---|---|---|---|---|---|---|---|
| 17 | Quil A 10 μg/dose | PR8 | 0.1 | 32 (11–67) | 226 (111–558) | −1.9 | 100 |
| 18 | Split virus | PR8 | 0.1 | 1 (0–23) | 3 (0–55) | −14.2 | 57 |
| 19 | Split virus | PR8 | 1 | 2 (0–150) | 4 (0–502) | −14 | 100 |
| 20 | Sham (PBS) | PR8 | 0 | 0 (0–2) | 0 | −24.5 | 14 |
| 21 | Sham (PBS) | PR8 | 0 | 0 (0–144) | 0 (0–3) | −26.4 | 14 |

[a]15 mice/group
[b]5 mice/group;
[c]10 mice challenge/group.

EXAMPLE 4

Immunogenicity Studies on Influenza Virus Protein Iscoms Formed from 703

In this experiment, sheep, 10 per group, were dosed twice by deep intramuscular injection, 4 weeks apart with disrupted virus (B/Panama) virus-iscoms or disrupted virus plus iscom matrix. All iscom vaccines contained 60 μg/dose QH703. Animals were bled immediately prior to the second dose of vaccine and again one week after the second dose. Sera were assayed by EIA for antibody to virus. The results are shown in the Table 5.

TABLE 5

Immunogenicity of QH703 influenza iscoms in sheep

|  |  | dose, HA | EIA Titre, Median (Range) | |
| --- | --- | --- | --- | --- |
| Group | Vaccine | μg | Primary | Secondary |
| 1 | Virus-iscoms | 10 | 43 (12–173) | 1694 (420–16803) |
| 2 | Virus + iscom-matrix | 10 | 11 (7–28) | 2197 (664–3544) |
| 3 | Virus | 10 | 2 (2–4) | 8 (3–28) |

EXAMPLE 5

Immunogenicity of QH703 DT-LHRH Iscoms in Cats

Cats were dosed twice at 4 week interval with 5 mg of a conjugate of diphtheria toxoid to which the decapeptide LHRH was coupled at a peptide to protein molecular ratio of 20:1. One group of 7 cats received conjugate alone, the other group of 7 cats received conjugate mixed with 100 μg QH703 iscom matrix. Results are presented in Table 6 for the estimation of antibody to the LHRH peptide, as measured by EIA. It can be seen that the QH703 iscom matrix has a significant adjuvant effect (p>.01), increasing the median titre 6 fold

TABLE 6

Immunogenicity of QH703 iscom matrix with DT-LHRH conjugate in cats.

ANTI LHRH ANTIBODY TITRE

| Group 1 - conjugate alone | Group 2 - QH703 iscoms plus conjugate |
| --- | --- |
| <20 | 230 |
| <20 | 287 |
| <20 | 314 |
| 70 | 427 |
| 90 | 440 |
| 115 | 780 |
| 315 | 793 |

EXAMPLE 6

IL-1 Induction by Various Mixtures of *Quillaja saponins*

Preparations of Quil A, QH-C and mixtures of QH-A and QH-C in the ratios 7.3 (=QH703), 5:5(QH505) and 3:7 (=QH307) were used to make iscom matrices according to standard procedures (see Example 3). These iscoms were dosed into mice subcataneously at doses ranging from 1 to 20 μg per mouse. Plasma samples were removed 8 hours later and tested for IL-1 by EIA. The results in FIG. 5 show that QH703 was significantly different to the other preparations in its ability to induce IL-1 production. It is considered that this response is a useful marker for the potential immunomodulatory activity of iscoms made from these various components and mixtures.

EXAMPLE 7

Haemolytic Activity of Quil A and Various QH Fractions and Mixtures

Assay Protocol

Human blood (20 ml) is collected in a lithium heparin blood collection tube, washed twice in a glucose citrate solution by centrifugation at 3000 g, 4° C. for 15 minutes then the red cells resuspended in glucose citrate solution.

Saponin solutions for testing are diluted by doubling dilution from 800 μg/ml in a 96-well microtitre tray. To each of these wells is added sufficient of a red blood cell suspension such that, if total haemolysis were to occur, the absorbance at 405 nm in an EIA plate reader would be around 1.0.

Saponin solution and red cells are mixed gently, incubated for 1 hour at 37° C. then the plates are centrifuged at 1000 g, 4° C. for 2 minutes then the absorbance at 405 nm read in an EIA plate reader. Results are expressed as the concentration of saponin preparation required to give 50% haemolysis. The higher the concentration required, the less haemolytic the preparation.

A number of different samples of QH-A, QH-B, QH-C and QH703 were tested for their haemolytic titre in solution and representative samples were used to prepare influenza iscoms and iscom matrix, which in turn were tested for haemolytic activity. The results are presented in Table 7. It can be seen that, in solution, QH703 has the haemolytic activity that would be expected from a mixture of QH-A and QH-C in those ratios. The order of activity from highest to lowest QH-B<QH-C<QH703<QH-A.

However, when these saponins are used to make iscoms, the degree to which the haemolytic activity is decreased is variable ranging from ~10 fold for QH-B and QH-C and 40 fold for QH-A and QH703. It is therefore demonstrated that the use of QH703 in iscoms is an optimal way to incorporate adjuvant active quantities of QH-C whilst minimizing the haemolytic activity of this saponin.

TABLE 7

Haemolytic activity of various saponins in solution and as iscoms

| | Haemolytic activity (μg/ml) | | | | | |
| --- | --- | --- | --- | --- | --- | --- |
| | In solution | | | Iscom | | |
| QH Fraction | no. tested | median | range | no. tested | median | range |
| A | 6 | 20 | 7–40 | 2 | >800 | — |
| B | 1 | 1 | — | 2 | 12.5 | 9–19 |
| C | 6 | 3 | 1–5 | 2 | 20 | — |
| 703 | 7 | 4 | 2–10 | 16 | 150 | 75–600 |

EXAMPLE 8

Pre-clinical Safety of QH703

QH703 as well as iscom matrix and immunogenic iscoms prepared from QH703 were subjected to pre-clinical toxicological and safety testing to prove their safety prior to the commencement of clinical studies in humans. Iscom matrix and influenza iscoms were prepared by the method of Example 3.

The following mutagenicity tests were conducted using QH703:

Ames test

Chromosomal aberration study using cultured mammalian cells

Micronucleus test in bone marrow of CD-1 mice

Mouse lymphoma mutation assay.

The following toxicological studies were conducted:

Single dose:

QH703 intramuscularly in rats

Iscom matrix prepared from QH703 intramuscularly in rats

Pyrogenicity of influenza iscoms prepared from QH703 in rabbits.

Repeat dose studies:

QH703 intramuscularly in rats, daily for 14 days

Iscom matrix prepared from QH703 intramuscularly in rats, daily for 14 days

Iscom matrix prepared from QH703, local tolerance in rabbits, 6 doses at 2 weekly intervals Influenza iscoms prepared from QH703, local tolerance in rabbits, 6 doses at 2 weekly intervals.

The conclusions from the mutagenicity studies with QH703 were that QH703 was not considered to produce mutagenic effects in the test systems used and was unlikely to produce any mutagenic effects in man.

The conclusions from the single dose toxicological studies were that it was difficult to clearly establish the "No Toxic Effect Level" in these studies, with QH703 and iscom matrix prepared from QH703 showing limited non-specific lethality in high doses (10 mg.kg$^{-1}$ and 1.4 mg.kg$^{-1}$ respectively). These doses represent greater than 1000 times the dose which is believed to be the maximum therapeutic dose.

The safety of QH703 and iscom matrix prepared from QH703 was confirmed in the other studies in rats and rabbits. At high doses, the effects which were observed could in part be contributed to the immunological (adjuvant) activity of the test material.

Influenza Iscom Vaccine was shown to be well tolerated in the rabbit local tolerance study for the full 6 doses, at doses of 100 μg of iscom matrix measured as QH703) per dose.

Pyrogenicity testing with a single 100 μg dose of Influenza Iscom Vaccine (measured as QH703) into rabbits has shown the vaccine to be non-pyrogenic.

EXAMPLE 9

Clinical Safety of Iscom Matrix Prepared from QH703 in Humans

Healthy male and female volunteers aged between 18 and 45 years of age who satisfied the inclusion/exclusion criteria for the study were each injected intramuscularly with 0.5 ml containing one of the following preparations in a single blind placebo controlled trial;

(i) placebo (diluent)

(ii) 25 μg of iscom matrix prepared from QH703

(iii) 50 μg of iscom matrix prepared from QH703

(iv) 100 μg of iscom matrix prepared from QH703

(v) 200 μg of iscom matrix prepared from QH703.

Iscom matrix was prepared from QH703 by the method of Example 3. The conclusions from the study were that all four dose levels of iscom matrix prepared from QH703 were well tolerated in healthy male and female volunteers.

Persons skilled in this art will appreciate that variations and modifications may be made to the invention as broadly described herein, other than those specifically described without departing from the spirit and scope of the invention. It is to be understood that this invention extends to include all such variations and modifications.

REFERENCES

Cox, J. C. and Coulter, A. R. (1992), "Advances in Adjuvant Technology and Application", in Animal Parasite Control Utilizing Biotechnology, Chapter 4, Ed. Yong, W. K. CRC Press.

Dalsgaard, K. (1974), Arch. Gesamte Virusforsch, 44, 243.

Kensil, C. A., et al (1988), International Patent Application No. PCT/US88/01842.

Kensil, C. A. et al. (1991), J. Immunol., 146, 431.

Kersten, G. F. A. et al. (1990). "Aspects of Iscoms, Analytical, Pharmaceutical and Adjuvant Properties"; Thesis, University of Utrecht.

What is claimed is:

1. A saponin preparation comprising saponins of *Quillaja saponaria*, said preparation comprising from 50 % to 70 % by weight of Fraction A of Quil A and from 50% to 30% by weight of Fraction C of Quil A, wherein said Fraction A of Quil A elutes during semi-preparative HPLC at approximately 39% acetonitrile and said Fraction C of Quil A elutes at approximately 49% acetonitrile during semi-preparative HPLC.

2. A saponin preparation according to claim 1, comprising about 70% by weight of Fraction A and about 30% by weight of Fraction C.

3. An immunostimulatory complex (iscom) matrix, comprising a saponin preparation according claim 1, a sterol and optionally a lipid.

4. An iscom matrix according to claim 3, wherein the sterol is cholesterol.

5. An iscom matrix according to claim 3, wherein the lipid, when present, is a phospholipid.

6. An immunogenic iscom which comprises an iscom matrix according to claim 3, having at least one immunogen incorporated into or associated with said iscom matrix.

7. A vaccine composition which comprises, as the active component thereof, either (i) an immunostimulatory complex (iscom) matrix, comprising a saponin preparation comprising saponins of Quillaja saponaria, said preparation comprising from 50 % to 70 % by weight of Fraction A of Quil A and from 50 % to 30% by weight of Fraction C of Quil A, a sterol and optionally a lipid and at least one immunogen, or (ii) an immunogenic iscom which comprises a saponin preparation comprising saponins of *Quillaja saponaria*, said preparation comprising from 50 % to 70% by weight of Fraction A of Quil A and from 50% to 30% by weight of Fraction C of Quil A, a sterol and optionally a lipid having at least one immunogen incorporated into or associated with said iscom matrix; and further comprising one or more pharmaceutically acceptable carriers and/or diluents, wherein said Fraction A of Quil A elutes during semi-preparative HPLC at approximately 39% acetonitrile and said Fraction C of Quil A elutes at approximately 49% acetonitrile.

8. A method of eliciting or inducing an immune response in an individual, comprising administering to said individual an immunologically effective amount of a vaccine composition according to claim 7.

9. An iscom matrix according to claim 5, wherein said phospholipid is phosphatidyl choline.

10. A method of preparing an immunostimulatory complex (iscom) matrix, which comprises admixing a saponin preparation according to claim 1 and a sterol.

11. A method according to claim 10, wherein a lipid is admixed with said saponin preparation and said sterol.

12. A method according to claim 11, wherein said sterol is cholesterol.

13. A method according to claim 11, wherein said lipid is a phospholipid.

14. A method according to claim 13, wherein the phospholipid is phosphatidyl choline.

15. An immunostimulatory complex (iscom) matrix prepared by the method of claim 10.

16. An immunogenic immunostimulatory complex (iscom) which comprises an iscom matrix according to claim 15, in which at least one immunogen is incorporated.

* * * * *